a

US 7,365,049 B2

(12) United States Patent
Becker-Andre et al.

(10) Patent No.: US 7,365,049 B2
(45) Date of Patent: Apr. 29, 2008

(54) AFAMIN-CONTAINING COMPOSITIONS AND METHODS OF USE

(75) Inventors: Michael Becker-Andre, Nuremberg (DE); Hans Dieplinger, Innsbruck (AT); Charlotte Teunissen, Amersfoort (NL); Lidija Jerkovic, Graz (AT)

(73) Assignee: Vitateq Biotechnology GmbH, Innsbruck (AT)

( * ) Notice: Subject to any disclaimer, the term of this patent is extended or adjusted under 35 U.S.C. 154(b) by 169 days.

(21) Appl. No.: 10/476,236

(22) PCT Filed: Apr. 30, 2002

(86) PCT No.: PCT/AT02/00132

§ 371 (c)(1),
(2), (4) Date: Jun. 21, 2004

(87) PCT Pub. No.: WO02/087604

PCT Pub. Date: Nov. 7, 2002

(65) Prior Publication Data
US 2004/0235718 A1    Nov. 25, 2004

(30) Foreign Application Priority Data
Apr. 30, 2001  (AT) .............................. A 696/2001

(51) Int. Cl.
*A61K 31/00* (2006.01)
*A61K 38/00* (2006.01)
*A61K 31/355* (2006.01)
*A01N 61/00* (2006.01)
*A01N 37/18* (2006.01)
*A01N 43/16* (2006.01)

(52) U.S. Cl. .............................. 514/2; 514/1; 514/458; 514/879

(58) Field of Classification Search .................... 514/2, 514/458
See application file for complete search history.

(56) References Cited

FOREIGN PATENT DOCUMENTS

| WO | WO 95/27059 | 10/1995 |
| WO | WO 01/01148 | 1/2001 |

OTHER PUBLICATIONS

Grundman M. Vitamin E and Alzheimer disease: the basis for additional clinical trials Am J Clin Nutr 2000, 71(S), 630S-636S.*
Christen, "Oxidative stress and Alzheimer disease.," *Am. J. Clin. Nutr.*, 71(2):621s-629s, 2000.
Ebadi et al., "Oxidative stress and antioxidant therapy in Parkinson's disease.," *Prog. Neurobiol.*, 48(1):1-19, 1996.
Ghadge et al., "Mutant superoxide dismutase-1-linked familial amyotrophic lateral sclerosis: molecular mechanisms of neuronal death and protection," *J. Neurosci.*, 17(22):8756-8766, 1997.
Jerkovic et al., "Afamin and vitamin E in follicular fluid of patients undergoing IVF," *Human Reproduction*, 14(abstr. Book 1):203-204, 1999.
Jovanovic et al., "Biomarkers of oxidative stress are significantly elevated in down syndrome," *Free Radic. Res.*, 9:1044-1048, 1998.
Lichenstein et al., "Afamin is a new member of the albumin, alpha-fetoprotein, and vitamin D-binding protein gene family," *J. Biol. Chem.*, 269(27):18149-18154, 1994.
Mazel et al., "Doxorubicin-peptide conjugates overcome multidrug resistance," *Anticancer Drugs*, 12(2):107-116, 2001.
Peyser et al., "Trial of d-alpha-tocopherol in Huntington's disease," *Am. J. Psychiatry*, 152:1771-1775, 1995.
Post et al., "Induction of NF-kappaB activity during haloperidol-induced oxidative toxicity in clonal hippocampal cells: suppression of NF-kappaB and neuroprotection by antioxidants.," *J. Neurosci.*, 18(20):8236-8246, 1998.
Rouselle et al., "Enhanced delivery of doxorubicin into the brain via a peptide-vector-mediated strategy: saturation kinetics and specificity," *J. Pharmacol. Exp. Ther.*, 296(1):124-131, 2001.
Rousselle et al., "New advances in the transport of doxorubicin through the blood-brain barrier by a peptide vector-mediated strategy," *Mol. Pharmacol.*, 57(4):679-686, 2000.
Temsamani et al., "Brain drug delivery technologies: novel approaches for transporting therapeutics," *Phar. Sci. Technol. Today*, 3(5):155-162, 2000.
Teunissen et al., "Cognitive performance in combination with serum markers in an aging population: a 6 year follow-up study as part of the Maastricht Aging Study," *Society for Neuroscince Abstracts*, 26(1-2):abstract No. 575.3, 2000.
Chwatal, "Bilirubin binding stuides by means of enzymatic oxidation," *Molecular Analysis of a Human Plasma Protein of the Albumin Gene Family*, 1996 [translated].
Groenendijk et al., "apoAI-CIII-AIV gene cluster," *Atherosclerosis*, 157:1-11, 2001.
Jerkovic et al., "Afamin Is a Novel Human Vitamin E-Binding Glycoprotein Characterization and In Vitro Expression," *J of Proteome Research*, 4:889-899, 2005.
Karathanasis, "Apolipoprotein multigene family: Tandem organization of humans apolipoprotein AI, CIII, and AIV genes," *Proc Nat'l Acad Sci USA*, 82:6374-6378, 1985.
Lichenstein et al., "Afamin Is a New Member of the Albumin, alpha-Fetoprotein, and Vitamin D-binding Protein Gene Family," *J Biol. Chem.*, 269:18149-18154, 1994.
Mizejewski, "Alpha-fetoprotein Structure and Function: Relevance to Isoforms, Epitopes, and Conformational Variants," *Exp Biol Med*, 266:377-408, 2001.
Petersen et al., "Vitamin E and Donepezil for the treatment of mild cognitive impairment," *New England J Medicine*, 352:2379-2388, 2005.
van Dijk et al., "The role and mode of action of apolipoproteins CIII and AV: synergistic actors in triglyceride metabolism," *Current Opinon Lipdol*, 15:236-246, 2004.
Voegele et al., "Characterization of the Vitamin E-Binding Properties of Human Plasma Afamin," *Biochemistry*, 41:14532-14538, 2002.

* cited by examiner

*Primary Examiner*—John Pak
*Assistant Examiner*—Ernst V Arnold
(74) *Attorney, Agent, or Firm*—Fulbright & Jaworski, LLP

(57) ABSTRACT

The use of Afamin, in particular in combination with vitamin E is described for producing a preparation for the treatment of oxidative stress.

4 Claims, 5 Drawing Sheets

AFAMIN-CONTAINING COMPOSITIONS AND METHODS OF USE

This application is a U.S. national phase application under 35 U.S.C. § 371 of International Application No. PCT/AT02/00132 filed 30 Apr. 2002, which claims priority to Austrian Application No. A 696/2001 filed 30 Apr. 2001.

The invention relates to preparations of vitamin E in combination with Afamin.

Afamin is a 87 kDa protein which belongs to the albumin group and structurally and biochemically has many things in common with the proteins of this group, i.e. with human serum albumin, human α-fetoprotein or human vitamin D binding protein. Afamin has already been cloned and sequenced and thus is also available in recombinant form (WO 95/27059).

Apart from its sequence homologies, little is known about the function of Afamin. The possibility has been discussed that Afamin has sterole binding sites, yet probably does not bind actin. Due to an existing, yet not overwhelming similarity between Afamin and albumin, it is doubted that these proteins bind the same ligands (Lichenstein et al., The Journal of Biological Chemistry, 269 (27) (1994), pp. 18149-18154).

Biochemical and physiological examinations have shown that Afamin has vitamin E-binding properties and does not only occur in blood, but also in other body or organ fluids, such as, e.g., cerebrospinal, follicular and seminal fluid. The use of Afamin for determining the fertility of mammals has been described in WO 01/01148 A1.

Vitamin E or the vitamin E-group is used as a collective term for fat-soluble, naturally occurring compounds having a chroman structure and a $C_{16}$ side chain (tocopherols). Tocopherols are chroman-6-ols (3,4-di-hydro-2H-1-benzopyran-6-ols) which are substituted in position 2 with a 4,8,12-trimethyltridecyl residue. Tocopherols are slightly yellowish-reddish oily liquids that are insoluble in water, yet soluble in fats and oils, as well as in the usual solvents for fats. It is differentiated i.a. between α-, β-, γ-, δ-, and ε-tocopherols, the latter still having the original unsaturated phenyl side chain, as well as α-tocoquinones and hydroquinones in which the pyrane ring system is opened. The most frequent and most effective natural tocopherol is the α-tocopherol (2R, 4'R, 8'R)-form (trivial name: RRR-α-tocopherol) which is synthetically accessible like all other stereoisomers (Römpp Chemie-Lexikon, $10^{th}$ Edition, pp. 4572/4573 and 4878-4886).

Originally described as an anti-sterility vitamin, today the opinion prevails that the vitamins of group E mainly act as a scavenger of hyperoxide and peroxide radicals, as an antioxidant for unsaturated fatty acids for LDL, for vitamin A and carotenes. Vitamin E is also attributed an important role in inhibiting inflammations and in the immune function.

Therefore, vitamin E preparations are mainly used in circulation-stimulating and lipid-lowering agents for humans and animals.

The invention has as its object to provide new medical applications for Afamin. Moreover, vitamin E preparations having an improved activity, in particular as regards their antioxidant properties, are to be provided.

According to the invention, this object is achieved by a preparation containing Afamin, in particular in combination with vitamin E, which can be used to produce a preparation for the treatment of oxidative stress, in particular for the treatment of neurodegenerative diseases. According to the invention, surprisingly it has been found that by combining vitamin E and Afamin, a vitamin E preparation with improved properties can be provided, in particular a vitamin E preparation having an increased antioxidant action.

Even though a number of the most varying functions has been postulated for Afamin (primarily as a transporting system for fatty acids, hormones, enzymes, dyes, trace metals and medicaments, as well as a direct antioxidant (cf. WO 95/27059)), it has additionally shown according to the invention that Afamin itself (even without vitamin E) has a neuroprotective function which is increased by a surprising synergistic effect with vitamin E. Accordingly, primarily the combination preparation of Afamin and vitamin E according to the invention can be provided for the treatment of oxidative stress for a wide range of applications. According to the invention, it has been shown that the combination of Afamin and vitamin E is particularly well suited for the treatment of neurodegenerative diseases which are associated with oxidative stress.

This has been surprising insofar as up to now it has not been possible to confirm the previously postulated applications for Afamin (cf. WO 95/27059, in which i.a. the use for rheumatoid arthritis, ARDS, sepsis, arteriosclerosis etc. have been considered possible, yet without being capable of providing proof of the same or presenting plausible model test). It has been the more unexpected that Afamin, primarily in combination with vitamin E (and not, e.g., in combination with vitamin D, a known binding partner of another protein from the albumin group) exhibits a significantly improved antioxidant effect, as compared to the individual components.

By vitamin E, according to the invention, all the natural and synthetic biologically active tocopherol preparations as initially described are to be understood, in particular tocopherol preparations derived from natural sources, in particular from vegetable oils, such as, e.g., soy, wheat, maize, rice, cotton, alfalfa and nuts, as well as from fruit and vegetable, e.g. raspberries, beans, peas, fennel, bell peppers, black salsifies and celery. Also the synthetically produced tocopherol preparations, including the derivatives thereof, such as, e.g., tocopheryl acetate, -succinate, -nicotinate and -poly (oxyethylene)-succinate are usable within the scope of the present invention (cf. Römpp Chemie-Lexikon, pp. 4572/4573).

By Afamin, according to the invention all polypeptides which have a biological activity in common with the natural Afamin are to be understood, in particular various glycosylated, deglycosylated, non-glycosylated, lipidated or de-lipidated forms, as well as variants of Afamin prepared by recombinant technologies. A detailed structural definition of Afamin is, e.g., given in WO 95/27059 which is expressly included herein by reference thereto. In addition, recombinantly or proteolytically produced isolated sub-domains as well as chemically derivatized or modified forms (e.g., by acetylation, e.g. on lysine side chains) and recombinantly or chemically produced extended versions of the protein, e.g. by attaching functional peptides which enhance the crossing of the blood-brain barrier (as described, e.g., in Mazel et al. (Anticancer Drugs 12(2) (2001), 107-116), Temsamani et al. (Pharm. Sci. Technol. today 3(5) (2000), 155-162), Rousselle et al. (Mol. Pharmacol. 57(4) (2000) 679-6866), Rousselle et al. (J. Pharmacol. Exp. Ther. 296(1) (2001), 124-131) included.

Free radicals are involved in a number of acute and chronic neurological disorders, in particular in focal ischaemia, trauma, epilepsy, Huntington's Disease, Alzheimer's Disease, amyotropic lateral sclerosis (ALS), AIDS, dementia and other neurodegenerative diseases. Furthermore, there exists an increasing number of examinations which suggest a participation of reactive oxygen species (ROS) in traumatic brain injuries. Also the impaired sensitivity of various receptor systems with increasing age indicates an increasing deterioration of the reactions to oxidative stress.

Glutamate-induced cytotoxicity is a useful model system for testing compounds as regards their antioxidant activity (Kabayashi et al., Free Radic Res., 32 (2000), 115-124). Glutamate-induced cytotoxicity in Ht-4neuronal cells has been attributed to oxidative stress caused by the reduction of cellular glutathione. Glutamate induces apoptoses in cortical rat neurons and in the hippocampus-HT-22 cell line from mice by blocking the cystein uptake, whereby intracellular glutathione is reduced. This in turn results in the enrichment of ROS. A low concentration of α-tocopherols proved to be highly effective to protect the neuronal cells against cytotoxicity.

Neuropathologies of Huntington's Disease are caused by an excessive activation of glutamate-coupled ion channels, whereby neurons are killed by oxidative stress.

α-Tocopherol might prevent oxiradical damage of the cell membrane, and a slowing down of the course of Huntington's Disease has been discussed for such preparations. In particular, an antioxidant therapy might slow down the rate of reduction of the motor abilities in the course of Huntington's Disease (Peyser et al., Am. J. Psychiatry, 152 (1995), 1771-1775).

The expression of two mutant superoxide dismutases (SODs) associated with familial ALS cause the death of differentiated PC12 cells, upper cervical ganglia neurons and pyramidal neurons in the hyppocampus (Chadge et al., J. Neurosci, 17(22) (1997), 8756-8766). At cell death, many characteristics which are typical of apoptosis could be found. This cell death might be prevented by an efficient treatment with vitamin E (Chadge et al., J. Neurosci, 17(22) (1997), 8756-8766).

The striatum contains a high concentration of oxidatable dopamine. An older organism exhibits a reduced capability of answering to oxidative stress, whereby this region becomes very susceptible to damage caused by free radicals. Dopamin neurons are especially susceptible to such damage and diseases. A loss of Dopamin-neurons is associated with Parkinson's Disease, e.g., and in that instance harmful oxygen-free radicals are accumulated. α-Tocopherols might protect cells against cytotoxic effects caused by Dopamine and L-Dopa (Ebadi et al., Prog. Neurobiol. 48(1) (1996), 1-19).

There also exists convincing epidemiologic and in vitro evidence that chronic oxidative stress occurs in persons afflicted with Down syndrome (Javanovic et al., Free Radic Res., 9 (1998), 1044-1048). Such patients develop an Alzheimer-like change in the brain, starting at an age of from 30 to 40 years. In in vitro studies it could be shown that the reduced viability of Down syndrome neurons can be changed by antioxidants, such as vitamin E. The uptake of such oxidants with the food alone does not seem to cause a sufficient change, or improvement, respectively, as regards the biomarkers for oxidative stress.

Oxidative damage has also been associated with acute degenerative diseases, such as epilepsy, trauma and cerebral ischaemic conditions, such as, e.g., in strokes. In these neurological disorders, the antioxidant therapy has always been considered as suitable, yet so far efficient means therefor have been missing.

Haloperidol, a dopamine receptor antagonist, is often prescribed for the treatment of schizophrenia and other affective disturbances. Oxidative stress is considered as one of the main clinical side effects of haloperidol. This compound is lethal for HT22 cells of mouse hippocampus in a concentration-dependent manner and causes the cell death by oxidative stress. HP-induced oxidative cell death can best be prevented by vitamin E preparations (Post et al., J. Neurosci, 18(20) (1998), 8236-8246); Sagara, J. Neurochem. 71(3) (1998), 1002-1012). On molecular level, haloperidol specifically induces the activity of the Redox-sensitive transcription factor NF-κB. This intensified NF-κB activity could be blocked by neuro-protective antioxidants.

Even though the effects of antioxidant enzymes are contradictory in Alzheimer's Disease, changes in the glutathione-peroxidase or superoxide-dismutase activities have been observed by many researchers, and there are many hints suggesting that oxidative stress also plays an important role in Alzheimer patients. Above all, it could be shown that substances which are capable of scavenging free radicals, such as vitamin E, Selegilin and ginkgo biloba extract Egb 761, exhibit a positive effect in the therapeutic treatment of Alzheimer patients (Christen, Am. J. Clin. Nutr., 71(2) (2000), 621s-629s).

For these reasons, the Afamin according to the invention, particularly the combination preparation of Afamin and vitamin E, preferably is employed for the treatment of Alzheimer's Disease, Huntington's Disease or the amyotropic lateral sclerosis.

The combination preparation according to the invention thus is particularly useful for the treatment of neurodegenerative dementias, such as they occur with these diseases, e.g.

According to a further embodiment, the present invention relates to the use of Afamin, in particular in combination with vitamin E, for producing a preparation for the treatment of acute neurodegenerative diseases, in particular for the treatment of epilepsy, trauma and cerebral ischaemia (a stroke, e.g.).

For the reasons set out above, Afamin, or the combination preparation according to the invention, respectively, is also suitable for the treatment of Parkinson's Disease or for the treatment of the changes occurring in patients afflicted with Down syndrome, which changes are similar to Alzheimer's Disease.

According to another aspect of the present invention, also oxidative stress occurring as a side effect of a medicament treatment can be prevented with Afamin, or with the combination preparation according to the invention. In doing so, the Afamin, or the combination preparation according to the invention, can be provided together with the respective medicament, or it may be administered separately.

For all these indications, a positive therapeutic or prophylactic effect has already been described or at least plausibly been postulated by the experts in this field. With the combination preparation according to the invention with which the antioxidant effect of vitamin E preparations is decisively improved, according to the invention these indications can be treated or prevented more efficiently or at least their progress can be retarded.

Afamin, or the combination preparation according to the invention can be used for all these diseases both therapeutically and prophylactically, whereby the onset of the classically found symptoms can be prevented, or the course of the disease is retarded, respectively. Accordingly, the present invention also relates to the use of Afamin, or of the inventive combination preparation, respectively, for producing a neuroprotective preparation.

In a further aspect, the present invention relates to the use of Afamin, in particular in combination with vitamin E, for producing a preparation for the treatment of infertility disorders. According to the invention, it has been shown that infertility disorders can efficiently be treated with the help of Afamin. Furthermore, vitamin E, which originally has become known as a fertility factor, can decisively be improved in its per se known fertility effect by a combination with Afamin.

According to a further aspect, the present invention relates to a vitamin E preparation having an increased antioxidant effect, which is characterized in that it contains Afamin in addition to a vitamin E preparation produced from synthetic or natural sources. Preferably, Afamin and vitamin E have a molar ratio of between 20 to 100 vitamin E/Afamin. This ratio takes into consideration the theoretical maximum loading of an Afamin molecule by 18 molecules of vitamin E (cf. FIG. 3). In particular, Afamin can be used which is derived from recombinant sources, which may differ from natural, human Afamin e.g. in its mode of glycosylation, its lipid content or even in its amino acid sequence.

Besides the usual pharmaceutical carrier substances, also further pharmaceutically effective components may be admixed to the preparation according to the invention, e.g. components which are already known for a certain indication.

The invention will now be explained in more detail by way of the following examples and the drawing figures to which, of course, it shall not be restricted. Therein, FIG. 1 shows the glutamine synthetase activity after a 5-day treatment with 3-NP in the presence of various protective substances;

EXAMPLES

Example 1

3 NP(3-nitropropionic acid)-induced Reduction of Glutamine Synthetase (GS) Activity Because of the mechanistic and pathological similarities between 3-NP lesions and Hungington's Disease (HD), 3-NP has been proposed as an alternative HD-model. Malonate and 3-NP are inhibitors of the succinate dehydrogenase which produce an energy loss and lesions which are similar to those observed in HD. Systemic administration of 3-NP causes a progressive locomotory deterioration which corresponds to that of HD. 3-NP causes a highly selective striatal degeneration. It differs mechanistically from excitotoxic lesions in that 3-NP irreversibly inhibits the mitochondrial citrate cycle and leads to reduced ATP values and increased lactate concentrations.

Assay:

After the extraction of brain spheroids and a one-week culturing, D,L-alpha-tocopherol (0.1 mM) were added to the medium. Two weeks old spheroids were plated in a plate having six wells. Shortly after the exposure, the medium was replaced by 2 ml of fresh medium. The spheroids were exposed to 3-NP (0.5 and 5 mM, pH adjusted to 7 to 8), or to the protectors vitamin E (0.1 mM), glutathione (1 mM), DTT (0.25 mM), L-NAME (N(G)-nitro-L-alanine-methylester) (0.1 mM), Afamin (without vitamin E (0.3 and 3 µg/ml) or combinations of 3-NP with the protectors for 5 days. After 2 days, freshly prepared 3-NP and protectors were added to the medium (Mathews et al., J. Neurosci, 18(1) (1998), 156-163); Borlongan et al., Neurosci Biohav. Res. 21(3) (1997), 289-293).

Figure 1:
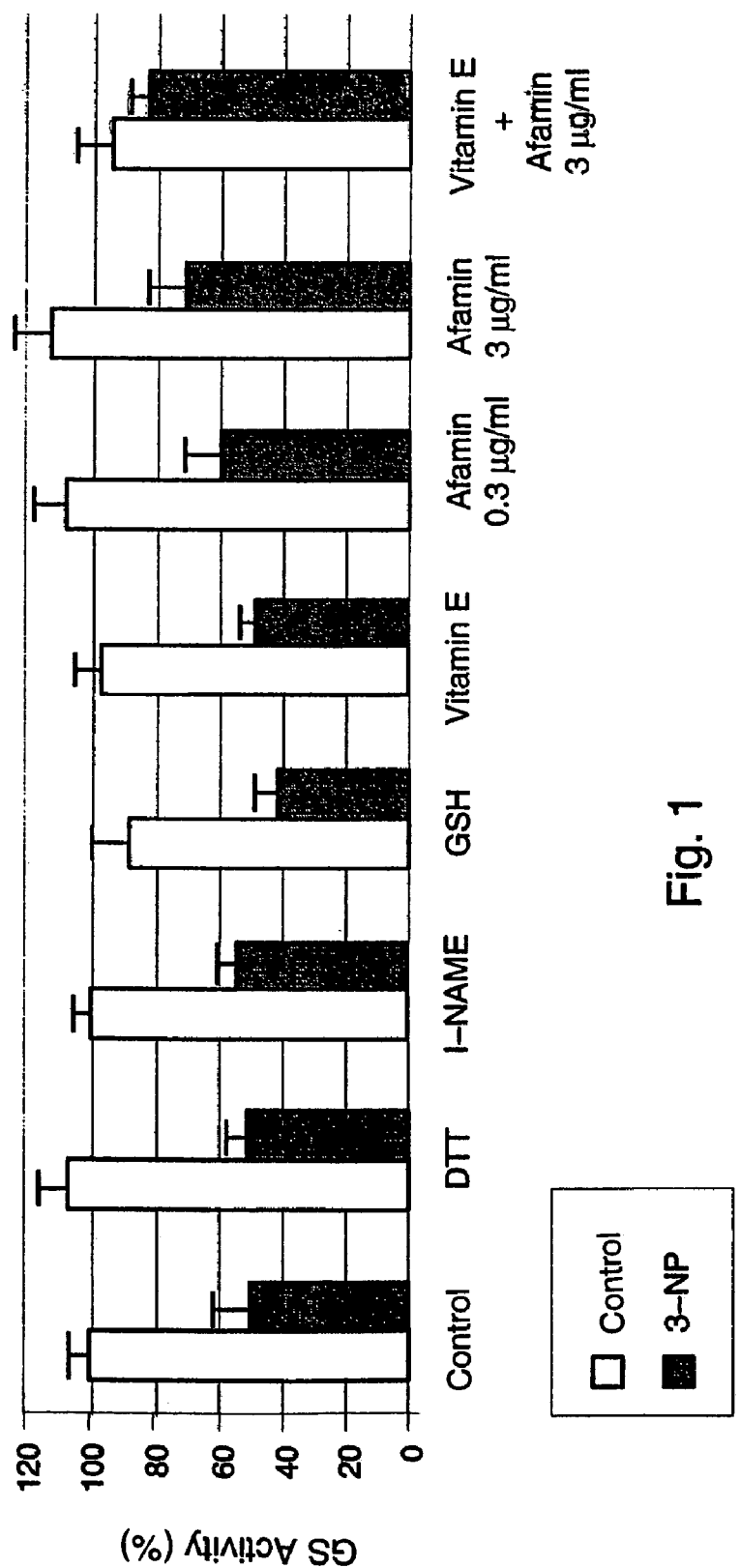

The results are illustrated in FIG. 1. Here it is shown that Afamin had by far the highest effect of all the tested substances in protecting the glutamine synthetase (GS, an astrocytic enzyme which is highly sensitive to oxidative stress) against inactivation by 3NP. As mentioned before, this system with 3NP constitutes a recognized model for excitotoxicity and serves as a model for Huntington's Disease.

Example 2

Neuroprotective Effect in Isolated Cortical Neurons of Chicken Embryos

The neuroprotective effect of Afamin was examined by assaying isolated cortical neurons of chicken embryos. The effect of Afamin was tested in a low-serum assay and in two lesion assays, namely in a β-amyloid and a $H_2O_2$-lesion assay.

After the low serum assay or the lesion assay, the MTT assay is used to check the viability of neuronal cells (MTT=3-(4,5-dimethylthiazol-2-yl)-2,5-diphenyltriazolium bromide). This is a suitable model which is extremely reproducible. The test also allows for assaying a large number of samples, and dose-dependent differences in the activity of a substance can be evaluated.

The neuronal viability of cells in vitro can be determined by means of this calorimetric MTT test. The MTT assay is based on the metabolic reduction of MTT, a substance of yellow color, to dark-blue formazane crystals by mitochondrial dehydrogenases (e.g. succinate dehydrogenase). The crystals are dissolved, and the spectrometric absorption is measured at a suitable wave length. It could be demonstrated that dead cells are not capable of cleaving MTT; dormant cells produce less formazan, therefore this assay can be used for quantifying the viability of cells, since this reaction is only catalyzed by live active cells (Mosmann et al., J. Immunol. Meth. 65(1983), 55; Bernabei et al., Hemat. Oncol. 7 (1989), 243; Barltrop et al., Bioorg. & Med. Chem. Lett. 1 (1991), 611; Cory et al., Cancer Commun. 3 (1991), 207).

In detail, isolated cortical neurons of 8- (lesion assays) or 9- (low serum assay) day-old chicken embryos (White Leghorn or Lohman Brown Hybrid strain) were used.

The neurons were prepared by breaking ethanoltreated eggs and putting the embryos into a plastic dish. After decapitation, the hemispheres were removed and collected. Loose tissue and meningial membranes were removed, and the hemispheres were mechanically dissociated.

80 µl cell suspension containing $6 \times 10^5$ cells/ml nutrient medium were added to each well of the microtiter plate which already contained 80 µl of medium with or without the substances. The plates were kept at 37° C., 95% humidity and 5% $CO_2$ without a change of media (up to 8 DIV).

The low serum medium contains 100 ml of DEMEM with 1 g of glucose/l, 2% fetal calf serum, 0.01% Gentamycin and 2 mM L-glutamine. The nutrient medium for the lesion assays contains 100 ml of DMEM with 4.5 g of glucose/l, 5% fetal calf serum, 0.01% gentamycin and 2 mM L-glutamine.

At DIV 8, the cells were treated with 20 μM of pre-aggregated β-amyloid peptide (Aβ$_{25-35}$; Sigma) for 72 hours, or with 100 μM $H_2O_2$ for 24 h.

At the end of each experiment, the viability of the cultures was tested by means of the MTT assay with a plate reader at 570 nm.

Figure 2A:
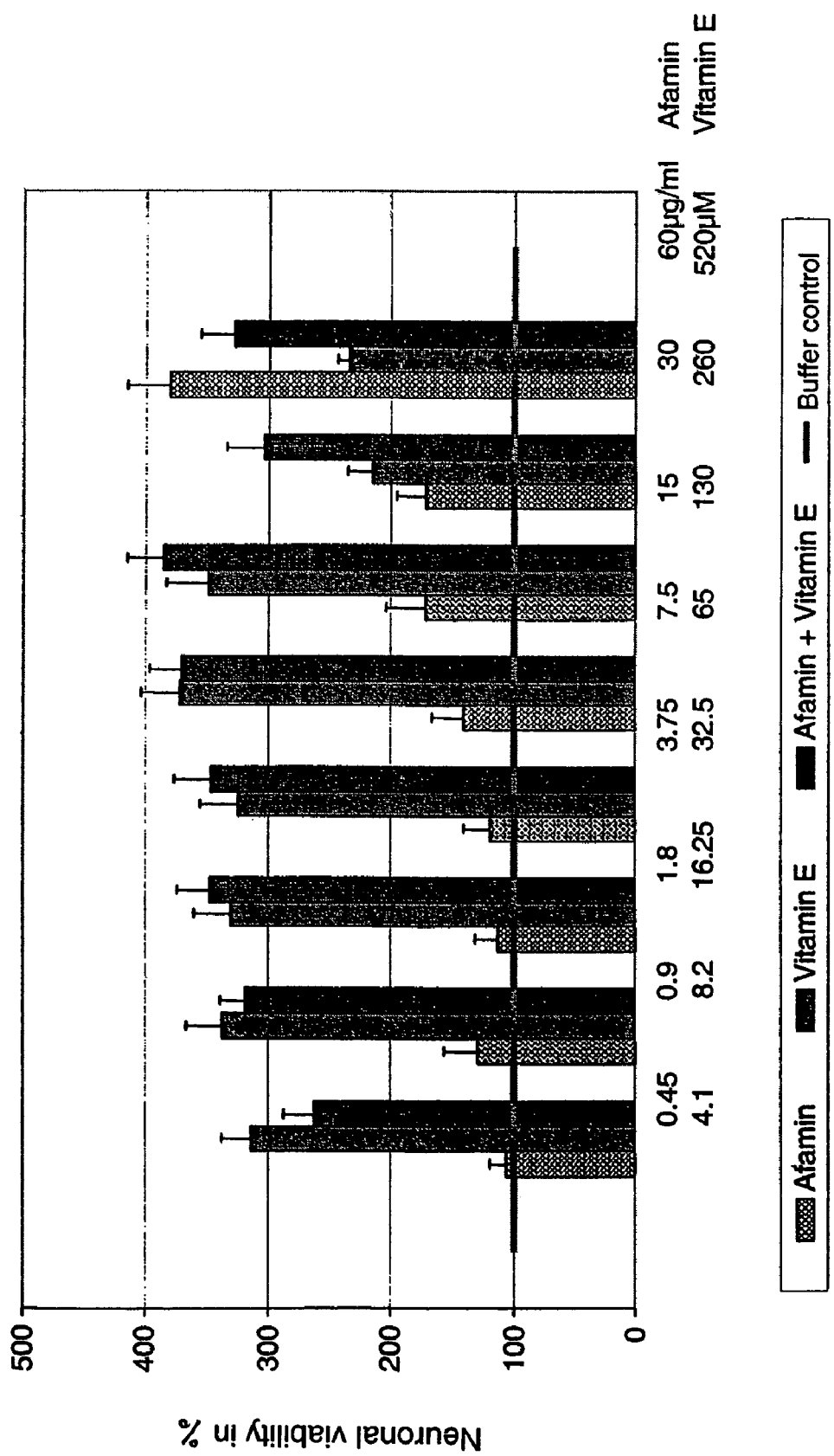
FIG. 2a shows Afamin and the combination of Afamin with vitamin E which protects against neuronal cell death, triggered by partial serum withdrawal to 2%.
Figure 2B:
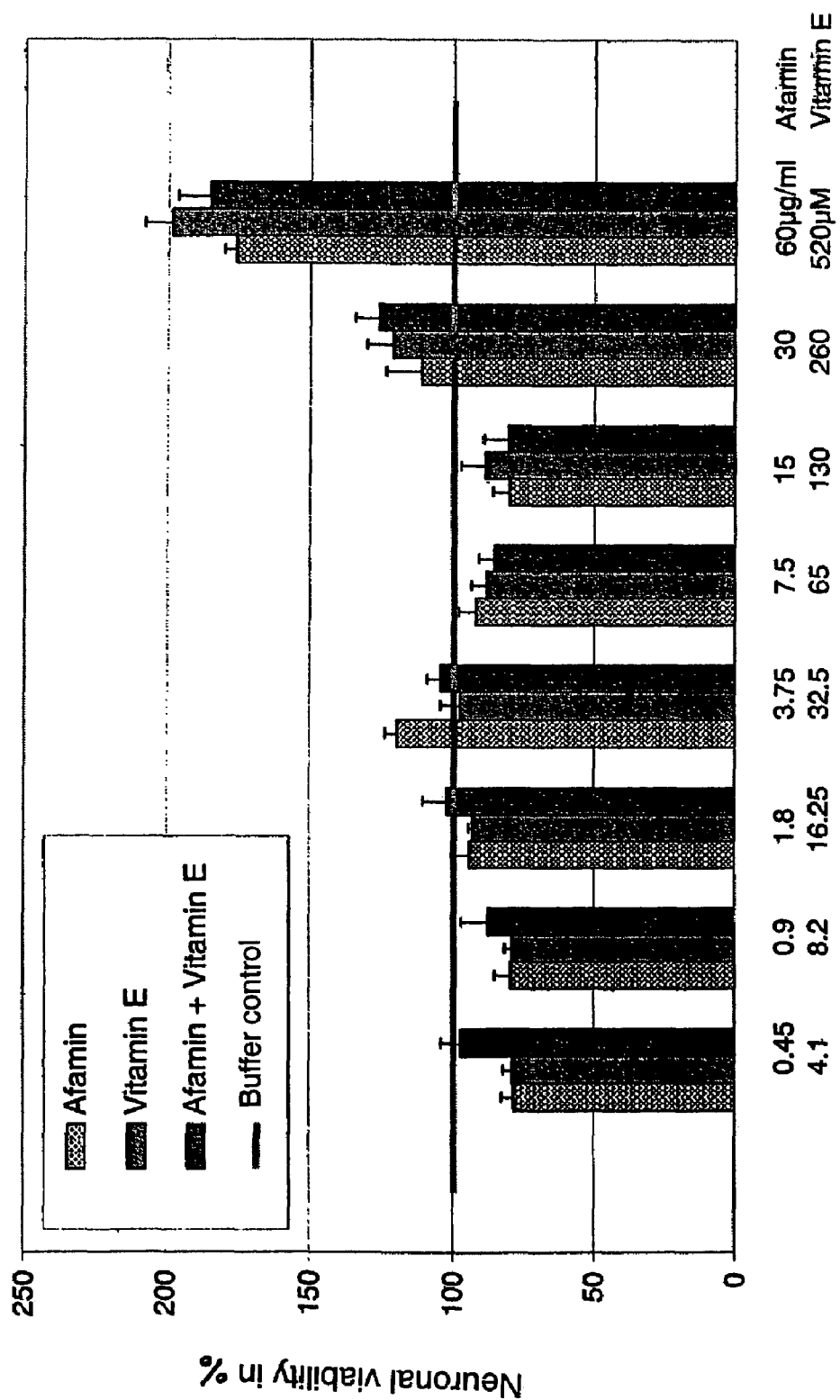
FIG. 2b shows Afamin and the combination of Afamin with vitamin E which protects against neuronal cell death, triggered by 100 µM $H_2O_2$.
Figure 2C:
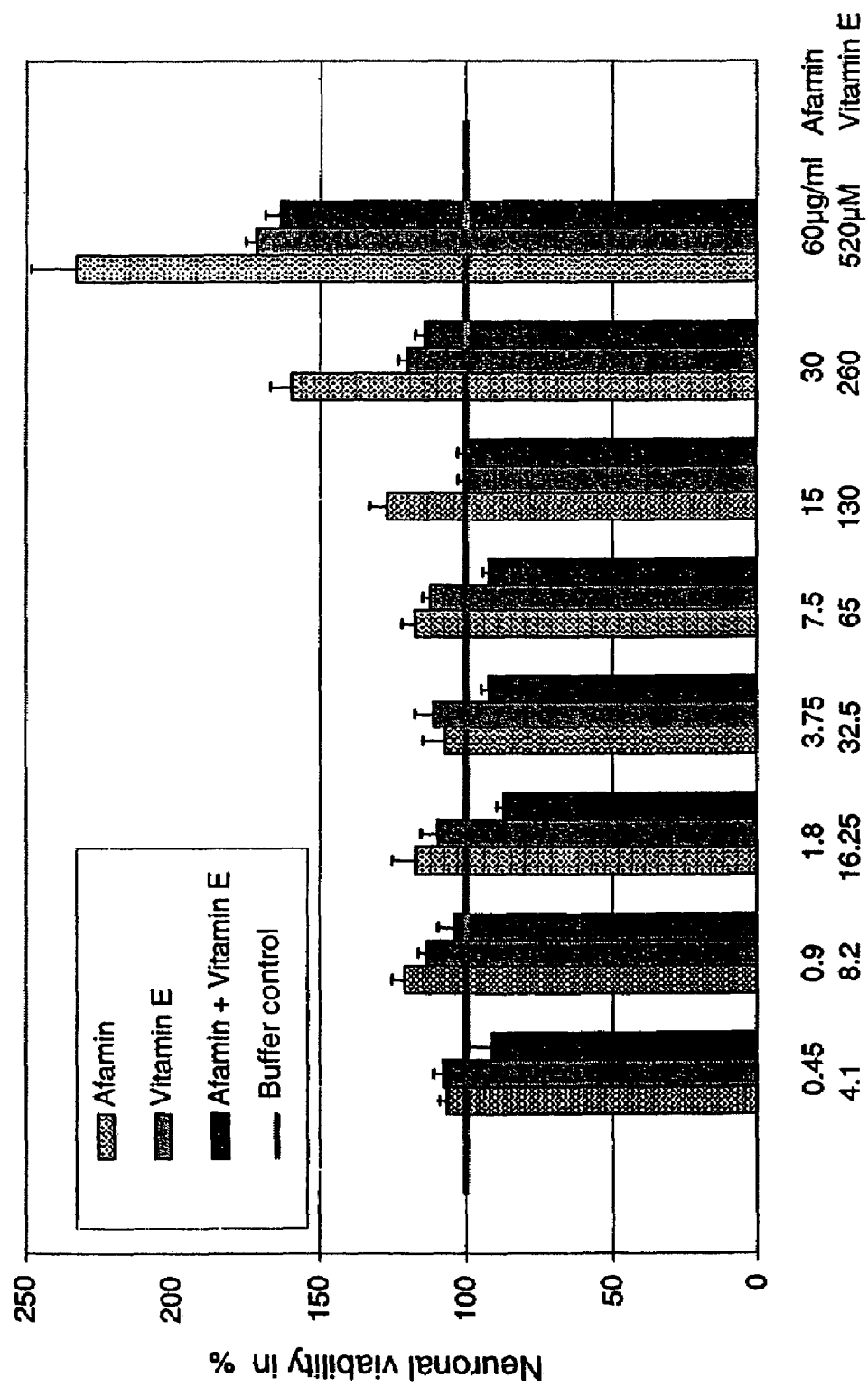
FIG. 2c shows Afamin and the combination of Afamin with vitamin E which protects against neuronal cell death, triggered by 20 µM pre-aggregated beta-amyloid peptide.
Figure 3:
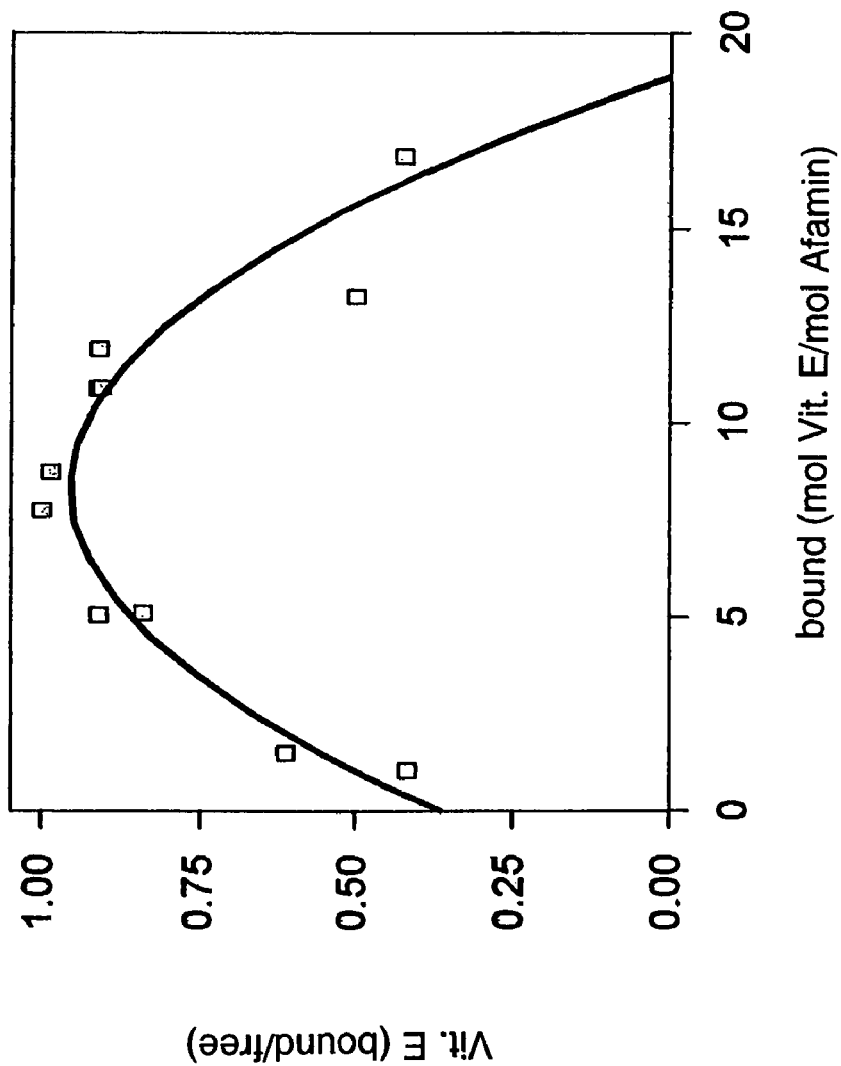
FIG. 3 shows a Scatchard-plot analysis of the binding of vitamin E to Afamin.

The results are illustrated in FIGS. 2a-c and show that Afamin, vitamin E and, above all, the combination of these two substances was capable of reducing the apoptosis in 2% low serum medium (FIG. 2a), and the damage by β-amyloid peptide or $H_2O_2$, respectively, which could be observed in control assays.

The invention claimed is:

1. A method of treating Alzheimer's disease comprising:
   obtaining Afamin; and
   administering an effective amount of the Afamin to a subject having Alzheimer's disease.

2. The method of claim 1, further comprising administering vitamin E to the subject.

3. The method of claim 2, wherein the Afamin and vitamin E are combined prior to administration.

4. The method of claim 1, wherein the Afamin is further defined as recombinant Afamin.

* * * * *

UNITED STATES PATENT AND TRADEMARK OFFICE
CERTIFICATE OF CORRECTION

PATENT NO. : 7,365,049 B2 Page 1 of 1
APPLICATION NO. : 10/476236
DATED : April 29, 2008
INVENTOR(S) : Michael Becker-Andre et al.

It is certified that error appears in the above-identified patent and that said Letters Patent is hereby corrected as shown below:

In title page, item (73) Assignee, line 1, delete "Vitateg" and insert --Vitateq-- therefor.

Signed and Sealed this

Twenty-ninth Day of July, 2008

JON W. DUDAS
*Director of the United States Patent and Trademark Office*